United States Patent [19]

Rasmussen et al.

[11] 4,251,437

[45] Feb. 17, 1981

[54] PROCESS FOR PRODUCING AN ANTIHEMOPHILIC FACTOR PREPARATION FROM HUMAN BLOOD PLASMA BY IRRADIATING WITH ELECTROMAGNETIC WAVES

[75] Inventors: Mirella E. Rasmussen, Copenhagen; Jørgen V. Jensen, Bagsvaerd; Jorgen F. Hansen, Rodovre, all of Denmark

[73] Assignee: Nordisk Insulinlaboratorium, Gentofte, Denmark

[21] Appl. No.: 88,671

[22] Filed: Oct. 26, 1979

[30] Foreign Application Priority Data

Nov. 1, 1978 [DK] Denmark ............................... 4875/78

[51] Int. Cl.$^3$ ................................................ C07G 7/00
[52] U.S. Cl. ................................. 260/112 B; 424/101; 424/177
[58] Field of Search ..................... 260/112 B; 424/101, 424/177

[56] References Cited

U.S. PATENT DOCUMENTS

| | | | |
|---|---|---|---|
| 2,867,567 | 1/1959 | Bidwell | 260/112 B X |
| 3,492,212 | 1/1970 | Searcy | 260/112 B X |
| 3,652,530 | 3/1972 | Johnson et al. | 260/112 B |

OTHER PUBLICATIONS

Nature, 203, 1964, p. 312, Pool et al.
Transfusion, Nov.–Dec. 1974, vol. 14, No. 6, pp. 595–597, Sherman et al.
J. Lab. Clin. Med. 67, pp. 23–32, Jan. 1966, Hershgold et al.

*Primary Examiner*—Howard E. Schain
*Attorney, Agent, or Firm*—Ladas & Parry

[57] ABSTRACT

An antihemophilic factor preparation (AHF) of high solubility and long half-life is produced in high yields by complete or partial thawing of deep-frozen human blood plasma by irradiation with electromagnetic waves of a frequency of about $10^8$–$10^{15}$ for a period of time and with an energy penetration such that the temperature in the thawed plasma does not exceed 10° C. at any point, and processing in a manner known per se by centrifuging the thawed product to form a cryoprecipitate, redissolving the cryoprecipitate in a buffer and isolating a concentrated solution which, if desired, is freeze-dried. Irradiation is preferably effected by microwaves of a frequency of $10^8$–$3 \times 10^{11}$ Hz, in particular $2 \times 10^9$–$3 \times 10^{10}$ Hz, or by infrared light, said frozen plasma being preheated if desired.

The preparation is suitable for injection performed by the patient himself without medical assistance.

7 Claims, No Drawings

PROCESS FOR PRODUCING AN ANTIHEMOPHILIC FACTOR PREPARATION FROM HUMAN BLOOD PLASMA BY IRRADIATING WITH ELECTROMAGNETIC WAVES

The present invention relates to a process for producing an antihemophilic factor preparation (AHF) by thawing deep-frozen human blood plasma, centrifuging the thawed product to form a cryoprecipitate, redissolving the precipitate in a buffer and isolating a concentrated solution which, if desired, is freeze-dried.

A very important property in normal blood is its ability to clot when it escapes the vessels in which it normally circulates, i.e. bleeding. Over the years extensive work has been done to elucidate the mechanisms that make blood clot. It is assumed that there is a plurality of components that participate in the coagulation system of the blood, and that there are 12 such components. The components are usually called coagulation factors with an added roman numeral I–XII.

Coagulation factor VIII, which this invention concerns, is also called antihemophilic factor (abbreviated AHF) and is a protein of a high molecular weight. It is present in very small amounts in blood plasma, its normal concentration being about 10 mg/l plasma.

The known and hereditary hemophilia, also called hemophilia A, is characteristic in that the biologically active coagulation factor VIII (AHF) is absent. Severe hemophilia means greatly increased bleeding tendency causing massive, sometimes even fatal bleeding from even the smallest cut. The disease manifests itself at a very early age, and many different complications may occur. For example, it is very common that patients have repeated bleedings in their joints, resulting in inflammation of the joints, which in the long run is tantamount to disablement. In this manner severely attacked hemophiliacs may become disabled already at the age of 20 if they are not constantly treated with preparation containing AHF.

It is known to produce AHF as preparations of low concentration (cryoprecipitate/intermediate purity) and as preparations of high concentration (high purity preparations).

The preparations of low concentration are in particular the so-called cryoprecipitates, i.e. the insoluble fraction obtained by freezing, which is present in blood plasma and remains insoluble when thawed at a low temperature. The cryoprecipitate contains essentially AHF and large amounts of fibrinogen.

Such thawing is usually performed by using water bath or by slow thawing in a room whose temperature is kept at 4° C. Following thawing only simple operations are carried out, such as filtration, centrifugation as well as freeze-drying, cf. J. Pool, E. K. Hershgold and A. Pappenhagen, Nature 203, 1964, p. 312. An approximately similar precipitate may be obtained by using the known Cohn's fractionation (fraction I-O). Here precipiration is effected by adding alcohol, and the obtained product comprises considerably more fibrinogen than the cryoprecipitate.

Cohn's fraction I-O is described by M Blombäck in Arkiv Kemi 12 (1958, p. 387). A combination of these two principles is described in the U.S. Pat. No. 3,652,530.

These methods produce a precipitate which, as mentioned, contains in particular AHF and fibrinogen, the latter in a rather large amount. The simple, but rather time-consuming process can give a fairly reasonable yield of 30–40% of the total content of AHF in the plasma, but the use of alcohol and the slow thawing of the frozen plasma denature AHF to some extent, leading to a reduction of the biological activity and thus the half-life, i.e. the time it takes for the biological activity to decrease to one half of its initial activity.

An essential drawback of these preparations, however, is their poor solubility, necessitating 35–100 ml of liquid to dissolve an amount of the preparation that corresponds to 500 units of AHF, and medical assistance is consequently required for the infusion.

An appropriate treatment of hemophiliacs requires already today, and will increasingly do so in the years ahed, that the patient himself can inject a dosage of the lacking blood factor (AHF). As the volumes that may be injected without medical assistance should not exceed 20–30 ml, such a product must have a high solubility so that about 500 units of AHF may be contained in a solution volume of 20–30 ml.

This may be achieved by the high purity preparations which may be produced from cryoprecipitates or Cohn's fraction I-O, as described above, where the extracted precipitate is purified in several steps, i.e. fibrinogen is substantially removed, cf. e.g. the U.S. Pat. No. 3,652,530.

Admittedly, it is possible to obtain preparations of a generally very high solubility by these methods, the solution volume required for dissolving 500 units of AHF varying from 15–25 ml according to the method used, but the methods suffer from very serious drawbacks, viz. a significantly reduced yield because it is only possible to isolate 10–20% of the AHF of the blood plasma, and a significantly decreased half-life which is only 4 to 5 hours, while the half-life of native AHF is 12 hours. This is of course extremely inexpedient owing to the limited amount of the starting material.

The object of the present invention is to provide a simple and rapid process for producing an AHF preparation in a high yield and of great solubility by thawing deep-frozen plasma and producing a cryoprecipitate from which AHF is isolated.

The invention is based on the recognition that extensive and prolonged processing of the blood plasma and its fractions are detrimental to the plasma proteins, and that the yield and solubility are therefore improved if thawing is effected and the cryoprecipitate is isolated in the shortest possible time under closely controlled temperatures and in the absence of chemical agents, minimizing the decomposition of AHF. It has been found that these requirements may advantageously be satisfied by performing the thawing step or at least the last part of it by irradiation with electromagnetic waves, preferably microwaves or waves in the infrared spectrum. The treatment is carried out while the plasma is still under sterile conditions in the bag in which it is frozen down, preferably a 200 ml bag.

It appears from the foregoing that besides being of importance for AHF the rapid thawing leaves all other plasma proteins undamaged so that processes directed against other plasma proteins also benefit from the method.

Accordingly, the invention provides a process for producing an antihemophilic factor preparation (AHF) by thawing deep-frozen human blood plasma, centrifuging the thawed product to form a cryoprecipitate, redissolving the precipitate in a buffer and isolating a concentrated solution which, if desired, is freeze-dried, said process being characterized by thawing partly or completely the frozen plasma by irradiation with electromagnetic waves of a frequency of about $10^8$–$10^{15}$ Hz for a period of time and with an energy penetration such that the temperature in the thawed blood plasma does not exceed 10° C. at any point.

It has surprisingly been found that the product was produced in a very high yield, up to 50% of the AHF of the blood plasma, that the half-life is increased and that the product has a very high solubility. Thus, it is possible to dissolve 500 units in a solution volume of 25 ml. It is assumed that a contributory factor is that the proposed thawing only slightly denatures AHF and fibrinogen, which means that their solubility characteristics are not impaired.

True, it has previously been realized that certain clinical situations, such as massive bleeding in open heart surgery, requires rapid availability of large amounts of blood plasma, and that supply of specific plasma components, such as cryoprecipitate, is not always sufficient to reverse a hemostatic defect in the patient. Consequently, large amounts of thawed plasma must be available because it takes a long time to thaw the plasma. This causes an undesirable deterioration of e.g. the coagulation factors of the plasma when it stands in a thawed state. To correct this, it has been proposed by Sherman and Dorner, Transfusion, Nov.–Dec. 1974, vol. 14, no. 6, p. 595–97 to thaw the necessary plasma by microwaves before use so that it may be immediately administered to the patient, or in other words to impart a temperature to it which is close to the patient's body temperature (37° C.) Sherman and Dorner have admittedly demonstrated by determination immediately after thawing that the coagulation factors of the plasma not are destroyed more than by conventional thawing at 37° C., which, however, in respect of the AHF factor (VIII) is as much as some 25% of the original amount. However, the sole aim of Sherman et al. was to show that all of the thawed plasma may be administered at an acute need without any risk, and they have not even suggested that the plasma is applicable for extracting the factors, but, on the contrary have stressed that it may be necessary to add further amounts of specific factors in special cases.

By way of comparison it may be mentioned that a factor VIII determination analogous with Sherman on a plasma thawed in accordance with the invention will reveal that 90–100% of the total content of factor VIII is present in the plasma. Of this about 60–70% enters into the cryoprecipitate, the balance remaining in solution in the cryosupernatant. Sherman aims, as will be appreciated, at an entirely different solution than production of AHF, and provides no direct inspiration in this regard. The artisan could not have predicted that it would be possible to control microwave thawing of blood plasma to produce a cryoprecipitate, because he would expect that the thawed part of the plasma would he heated to boiling owing to the wide difference in the dielectricity constant of water (thawed plasma) and ice (still frozen plasma). Such wide differences in temperature make it a priori inconceivable that the controlled temperature conditions necessary for the formation of cryoprecipitate can be kept. Sherman must necessarily bring all factors into solution as rapidly as possible and does not have to pay any attention to differences in the temperature in the plasma during thawing. In particular, the artisan could not have predicted that it was possible to obtain a readily soluble cryoprecipitate in a good yield.

The temperature of 10° C. represents the practical upper limit of maintaining a cryoprecipitate because it will dissolve at a higher temperature.

A suitable temperature range is −1° to 6° C., and it is advantageous that during irradiation the temperature does not exceed 4° C. at any point. This temperature provides a suitable, balanced, low solubility of the cryoprecipitate and an overall period of irradiation that may be decreased to some 4 or 5 minutes.

To facilitate the treatment with electromagnetic waves, preheating, e.g. up to 0° C., may be carried out to advantage, e.g. by leaving the bag containing the frozen plasma a suitable time, e.g. about 30 min. at room temperature, or in a refrigerator or in a water bath. Preheating may also be performed by irradiating the plasma bag with electromagnetic waves for a shorter or longer period. These irradiations may, if desired, be employed during the thawing process as well, where waves of the same or different frequencies may be used. Heating by microwaves may be accomplished in a commercially available microwave oven, e.g. Husquarna model 105 emitting microwaves of a frequency of 2450 MHz, which provides a sufficient penetration depth for the thawing to be completed in a suitably short time. The essential thing is merely that the overall radiation is carried out in such a manner that the average antenna effect (nominal effect generated) is sufficiently low for the temperature not to exceed 10° C. at any time. According to circumstances, irradiation may be effected at intervals or continuously.

The appropriate period of heating varies also according to the type of oven used, particularly its antenna effect, and the frequency used, as well as the form, degree of crushing and initial temperature of the plasma, and may be established by experiments. The preferred frequency is $2\times10^9$–$3\times10^{10}$ Hz.

The cryoprecipitate precipitated during thawing is processed in a manner known per se by centrifuging at a low temperature (−1° to +4° C.), redissolving in a suitable, physiologically acceptable buffer, e.g. a citrate glucose buffer, pH about 6.5.

The redissolved cryoprecipitate is filtered and may then be poured into infusion bottles in volumes corresponding to about 500 units of AHF, and may advantageously be freeze-dried. The finished preparation is completely redissolved before use in 25 ml of water and is therefore suitable for injection by the patient himself.

In the table below the preparation produced in accordance with the invention is compared with conventional, commercial preparations. The table shows that compared with the cryoprecipitate/intermediate purity preparations, the preparation of the invention is fully up to the standard of the best preparations in terms of yield and half-life. As regards solubility the present preparation is almost three times better than said, known preparation. Compared with the high purity preparations the preparation of the invention has a solubility which is on a level with theirs, while the yield and half-life are about three times better than those of the high purity preparations.

| Product | Yield in % | Concentration[2] units/ml | Volume required for dissolving 500 units/ml | half-life[1] in hours |
|---|---|---|---|---|
| Cryoprecipitate/intermediate purity preparations | 30-40 | 5-15 | 35-100 | 8-9[3] |
| High purity preparations | 10-20 | 20-40 | 15-25 | 4-5[3] |
| Preparation produced in accordance with the invention | 40-50 | 20 | 25 | 10-12 |

[1] For AHF in a native state the half-life is 12 hours.
[2] 1 unit = the content of AHF in 1 ml of fresh, normal, human blood plasma
[3] According to J. H. Smith, G. R. Miller, R. T. Beckenridge, JAMA, vol. 220, 1352 (1973)

The process of the invention will be described in more detail in the examples below.

EXAMPLE 1

The starting material used was frozen, human blood plasma contained in plastic bags of 200 ml each. The deep-frozen bags were heated by standing at room temperature for 45 min., and then their contents were crushed by a mechanical treatment. The bag was placed in a microwave oven, Husquarna microwave oven model 105 (2450 MHz). Four bags of 200 ml each were placed in each oven of the above type. After total thawing period of 4½ min. (7 cycles of 15 sec. pulse and 30 sec. pause each) the contents of the bags were thawed without the temperature having exceeded 4° C. The precipitated cryoprecipitate was centrifuged off (10,000 g, T=4° C., 15-20 min.), and was then redissolved in a citrate glucose buffer containing 0.5 g of citrate/l and 25 g of glucose/l. The pH=6.5 was adjusted by hydrochloric acid.

For each centrifuged precipitate there was used a volume of buffer corresponding to about 1/25 of the original blood plasma volume. the redissolved cryoprecipitate was then filtered by an 8 μm filter. After filtration the solution was poured into 100 ml infusion bottles, with 50 ml in each bottle.

Then the solution was spin frozen (−40° C.), and subsequently freeze-dried for 24 hours in a WKF freeze drier.

The finished preparation contained 500 E factor VIII (±20%) per bottle, which may be redissolved before use in 25 ml of water.

EXAMPLE 2

Thawing and processing were conducted as in Example 1, with the exception that the deep-frozen plasma was preheated by brief thawing in the microwave oven (2 cycles of 30 sec. pulse and 1 min. pause each). Processing yielded a freeze-dried preparation of the same fine solubility and strength characteristics as in Example 1.

EXAMPLE 3

Bags of the same type as used in Example 1 were placed in a deep-frozen state in the microwave oven and thawed completely by slow irradiation with brief microwave pulses (32 cycles of 5 sec. each, pulse and 55 sec. pause). The cryoprecipitate thus formed was processed as in Example 1 and resulted in a product of the same fine solubility and strength characteristics as in Examples 1 and 2.

EXAMPLE 4

Bags of the same type as in Example 1 were placed in a deep-frozen state in a microwave oven constructed to give off an antenna effect of about 10% of that of the oven used in Example 1. The bags were thawed by continuous microwave irradiation for some 30 min. The cryoprecipitate formed was processed as in Example 1 and resulted in a preparation of the same fine solubility and strength characteristics as in Example 1.

EXAMPLE 5

A plastic bag of about 200 ml of deep-frozen plasma was preheated by electromagnetic irradiation, in the infrared region, of an intensity of 2 W/cm$^2$ for 5 min.

Following preheating the contents of the bag were crushed by mechanical treatment, and the bag was again exposed to infrared radiation, now of an intensity of 0.5 W/cm$^2$. After some 15 min. the contents of the bag was suitably thawed, and then given the same treatment as in Example 1. The product produced had the same fine solubility and strength characteristics as in Example 1.

EXAMPLE 6

A plastic bag of about 200 ml of plasma was preheated analogously with Example 5 by infrared radiation of 2 W/cm$^2$ for 5 min.

Following preheating the contents of the bag were crushed and the bag was placed in the microwave oven employed in Example 1, and was thawed analogously with Example 1. The further processing as in Example 1 resulted in a preparation of the same fine solubility and strength characteristics.

We claim:

1. A process for producing an antihemophilic factor preparation (AHF) comprising the steps of thawing deep-frozen human blood plasma, at least partially, by irradiation with electromagnetic waves of a frequency of about $10^8$–$10^{15}$ Hz for a period of time and with an energy penetration such that the temperature in the thawed blood plasma does not exceed b 10° C. at any point, centrifuging the thawed product to form a cryoprecipitate, redissolving the cryoprecipitate in a buffer, isolating a concentrated solution, and optionally freeze-drying the concentrated solution.

2. A process according to claim 1, wherein the irradiation is controlled so that the temperature in the thawed product does not exceed 4° C. at any point.

3. A process according to claim 1, wherein the irradiation is carried out with microwaves of a frequency of about $10^8$–$3 \times 10^{11}$ Hz.

4. A process according to claim 1, wherein the irradiation is carried out with microwaves of a frequency of about $2 \times 10^9$–$3 \times 10^{10}$ Hz.

5. An antihemophilic factor preparation (AHF) of high solubility and long half-life which has been recovered by thawing deep-frozen human blood plasma, at least partially, by irradiation with electromagnetic waves of a frequency of about $10^8$–$10^{15}$ Hz for a period of time and with an energy penetration such that the temperature in the thawed plasma does not exceed 10° C. at any point, centrifuging the thawed product to form a cryoprecipitate, redissolving the precipitate in a buffer, isolating a concentrated solution and optionally freeze-drying said concentrated solution.

6. An antihemophilic factor preparation according to claim 5, wherein the thawing has been effected by irradiation with microwaves of a frequency of $10^8$–$3\times10^{11}$ Hz.

7. An antihemophilic factor preparation according to claim 5, wherein the thawing has been effected by irradiation with microwaves of a frequency of $2\times10^9$–$3\times10^{10}$ Hz.

* * * * *